United States Patent
Loncar et al.

(10) Patent No.: US 8,127,762 B2
(45) Date of Patent: Mar. 6, 2012

(54) ANAESTHESIA APPARATUS AND METHOD FOR OPERATING AN ANAESTHESIA APPARATUS

(75) Inventors: Mario Loncar, Ekerö (SE); Christer Ahlmén, Sollentuna (SE); Stefan Broborg, Haninge (SE)

(73) Assignee: Maquet Critical Care AB, Solna (SE)

(*) Notice: Subject to any disclaimer, the term of this patent is extended or adjusted under 35 U.S.C. 154(b) by 569 days.

(21) Appl. No.: 12/305,300

(22) PCT Filed: Jun. 29, 2006

(86) PCT No.: PCT/EP2006/063687
§ 371 (c)(1),
(2), (4) Date: Dec. 17, 2008

(87) PCT Pub. No.: WO2008/000299
PCT Pub. Date: Jan. 3, 2008

(65) Prior Publication Data
US 2009/0250054 A1   Oct. 8, 2009

(51) Int. Cl.
*A61M 15/00* (2006.01)
*A61M 16/00* (2006.01)
*A61M 16/10* (2006.01)

(52) U.S. Cl. ............ 128/203.12; 128/203.14; 128/910

(58) Field of Classification Search ............ 128/200.24, 128/203.12, 203.15, 205.27–205.29, 910
See application file for complete search history.

(56) References Cited

U.S. PATENT DOCUMENTS

| | | | |
|---|---|---|---|
| 4,791,922 A | 12/1988 | Lindsey-Scott et al. | |
| 5,398,675 A * | 3/1995 | Henkin et al. | 128/203.12 |
| 5,471,979 A | 12/1995 | Psaros et al. | |
| 5,678,537 A * | 10/1997 | Bathe et al. | 128/203.12 |
| 5,687,709 A | 11/1997 | Akersberg | |
| 5,694,924 A | 12/1997 | Cewers | |
| 5,699,788 A * | 12/1997 | Lekholm et al. | 128/203.12 |
| 6,131,571 A | 10/2000 | Lampotang et al. | |
| 6,152,133 A | 11/2000 | Psaros et al. | |
| 6,213,120 B1 | 4/2001 | Block et al. | |

* cited by examiner

Primary Examiner — Loan Thanh
Assistant Examiner — Oren Ginsberg
(74) Attorney, Agent, or Firm — Schiff Hardin LLP

(57) ABSTRACT

An anaesthesia apparatus has a control unit that controls a gas flow of a flushing gas through at least part of the anaesthesia apparatus so as to flush anaesthetic agent from the apparatus when the apparatus is not connected to a patient. In this way the remaining anaesthetic agent can be removed from the anaesthesia apparatus after use before connecting another patient. Pre-use check of the apparatus can be performed automatically.

22 Claims, 3 Drawing Sheets

ANAESTHESIA APPARATUS AND METHOD FOR OPERATING AN ANAESTHESIA APPARATUS

BACKGROUND OF THE INVENTION

1. Field of the Invention

The present invention relates to an anaesthesia apparatus and to a method for operating an anaesthesia apparatus. In particular the invention relates to an anaesthesia apparatus comprising a reflector filter for reflecting anaesthetic agent exhaled from the patient.

2. Description of the Prior Art

Anaesthesia apparatuses are known in the art for providing anaesthetics to patients. The term "anaesthesia apparatus" as used herein encompasses also sedation apparatuses, which are a simpler form of anaesthesia apparatus.

Anaesthesia apparatuses typically have inspiration and expiration lines for providing and withdrawing breathing gas from the patient and a vaporizer for providing anesthetic into the breathing gas flow. The vaporizer can be placed in the inspiration line or in a branch connected with the inspiration line, to provide vaporized anaesthetic to the breathing gas flow. The inspiration and expiration lines are interconnected near the patient in a so called Y piece, which is in turn used to connect the apparatus to the patient.

Anaesthesia apparatuses are usually provided with a manual ventilation system in parallel with an automatic mechanical ventilation system and a ventilation selection switch for selecting between the manual and the mechanical ventilation system. The manual ventilation system typically includes a manual ventilation bag that can be squeezed by medical personnel to provide air to the patient and be allowed to expand during exhalation.

The anaesthetic agent is typically added in a suitable dose to the breathing gas close to the patient, so that the patient inhales a suitable amount of anaesthetic. Not all the anaesthetic agent will be consumed by the patient. The part that is not consumed is exhaled during expiration. Some anaesthesia apparatuses, such as the apparatus de-scribed in U.S. Pat. No. 5,471,979, also have a reflector filter for anaesthetic. The filter adsorbs anaesthetic that is not consumed by the patient and during inhalation re-leases it again so that it is provided to the patient instead of being expired together with the expiration gas. Such filters enable more efficient use of anaesthetics.

U.S. Pat. No. 6,152,133 discloses an anaesthetic delivery system in which a reflector filter as discussed above is used. A supply of flushing gas is provided, to flush retained an-aesthetic from the filter while the system is connected to a patient, without passing the flushing gas to the patient. In this way the amount of anaesthetic retained in the filter from the expired gas can be varied on demand.

Between patients pre-use check must be performed. This is traditionally done manually according to recommended procedures such as the FDI "Anesthesia Apparatus Checkout Recommendations". Today this is typically done in a combination of manual and automatic steps, by running a self test program which for example re-quires occlusion of the Y piece at certain stages in the program. In the prior art this is done manually. Hence, the pre-use check requires the attention of an operator who must be available such as for occluding the Y piece when required by the self test program.

Also, between patients the system must be flushed, to ensure that there is no anaesthetic left in any of the filters or other units in the apparatus. This is particularly important if another anaesthetic agent is used for the next patient.

In conventional anaesthetic apparatuses it is sufficient to flush out the gas that is pre-sent in the breathing circuit of the system to ensure that all anaesthetics has been removed. In systems using a reflector filter, such as the ones disclosed in U.S. Pat. Nos. 5,471,979 and 6,152,133, the amount of anaesthetic agent retained in the reflector is much higher compared to the amount contained in the gas volume of the tubing. Thus, it is necessary to ensure that all of the anaesthetic agent that is present in the reflector filter is also flushed out before the apparatus is used again. Alternatively the whole filter must be replaced by a new filter, which is expensive and cumbersome. The cited documents do not propose any solution to this problem.

SUMMARY OF THE INVENTION

An object of the present invention is to provide an improved system and method for flushing anaesthetics from an anaesthetic system between patients, and self-test procedures for such a system.

This object is achieved according to the present invention by an anaesthesia apparatus having an inspiration line and an expiration line, the expiration line including a PEEP valve for controlling end-expiratory pressure. The inspiration and expiration lines are connectable to and disconnectable from a patient. At least one gas source provides breathing gas to the inspiration line. A vaporizer provides anaesthetic to the inspiration line. A first evacuation line evacuates expired gas. A control unit automatically controls the gas flow through at least part of the anaesthesia apparatus so as to flush anaesthetic agent from the apparatus when the apparatus is not in use.

The object is also achieved by a computer-readable medium encoded with programming instructions for controlling an anaesthesia apparatus as described above that, when run in a processor, controls at least some of the valves of the anaesthesia apparatus as to cause the anaesthesia apparatus to perform a pre-use check without the need for manual intervention.

The object is also achieved by a method of operating an anaesthesia apparatus when it is not in use, the anaesthesia apparatus having an inspiration line and an expiration line, the expiration line including a PEEP valve, and at least one gas source for providing breathing gas to the inspiration line, a vaporizer for providing anaesthetic to the inspiration line, and a common line for transporting breathing gas and expired gas, and an evacuation line for evacuating expired gas, and an evacuation system for evacuating gas flushed through the inspiration line when the anaesthesia apparatus is not connected to a patient. The method includes the steps of providing a gas flow of flushing gas through at least a part of the apparatus so as to flush anaesthetic agent from the apparatus when the apparatus is not in use.

According to the invention, therefore, the anaesthetic apparatus can be flushed of any anaesthetic agent between patients, without manual intervention.

The invention can be implemented in any kind of anaesthesia apparatus but is particularly useful in an anaesthesia apparatus comprising a reflector filter in the breathing circuit for reflecting exhaled anaesthetic agent during use, wherein the control means is arranged to control the gas flow through the reflector filter in such a way as to flush any anaesthetic agent from the filter when the apparatus is not in use. Since the major part of the anaesthetic agent left in the breathing circuit will be found in the reflector filter and the $CO_2$ absorber, it will be especially important to flush these units.

Preferably an internal gas analyzer is provided in the inspiration line for monitoring the concentration of anaesthetic in the gas and arranged to provide a signal indicative of the concentration to the control means. During the flushing phase/pre use check this gas analyzer can register the concentration of anaesthetic in the breathing gas and hence determine if it is safe to connect a new patient to the anaesthetic apparatus. If a reflector filter is used the gas analyzer can be used to determine if reuse of the reflector filter is safe. It can also determine if it is safe to dispose of the reflector filter and/or the $CO_2$ absorber.

In a first preferred embodiment the evacuation means comprises a second evacuation line connected to the patient end of the inspiration line and the expiration line for evacuation of the gas to a scavenging system, said second evacuation line including an evacuation valve.

The first embodiment is also feasible for pre-use check. The evacuation valve can be used during pre-use check to eliminate the need for operator action during pre-use check.

In the first embodiment the manual ventilation bag can be flushed after use and/or during pre-use check.

According to a second preferred embodiment the evacuation system has a carbon filter connectable to the patient end of the inspiration line for absorbing anaesthetic in the gas. The evacuation line can also be connected to the same carbon filter, instead of to a scavenging system. This is particularly useful if no scavenging system is available.

Typically, the anaesthesia apparatus further has a $CO_2$ absorber connected in the inspiration line for removing $CO_2$ in recirculated gas, the gas analyzer being connected between the absorbing filter and the patient end of the inspiration line.

In this case, the anaesthesia apparatus may further have a reflector filter for reflecting anaesthesia exhaled by the patient when the apparatus is used for providing anaesthesia to the patient. The reflecting filter is connected in the common line upstream of the split of the inspiration and expiration line. The apparatus further has an evacuation line for evacuating exhaled gas from the patient.

The anaesthesia apparatus may further have a manual ventilation system connected to the first evacuation line near the PEEP valve on the breathing system side.

The apparatus may further include a control unit that operates according to a computer program product as specified above.

DESCRIPTION OF THE PREFERRED EMBODIMENTS

Figure 1:
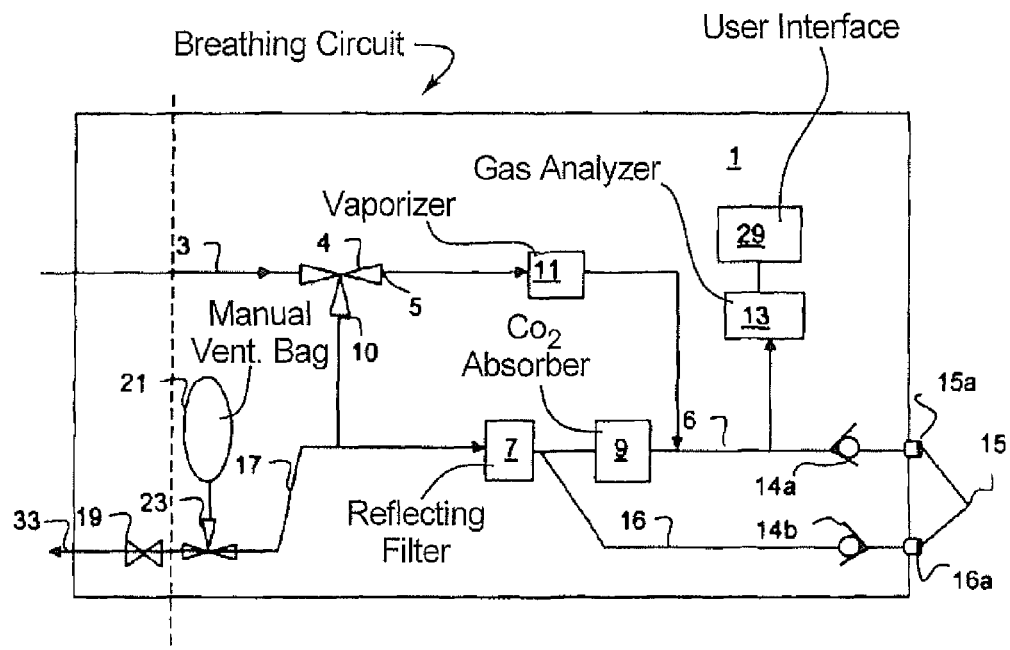
FIG. 1 shows an anaesthetic system for use with a patient.

FIG. 1 shows an anaesthetic apparatus. The breathing circuit 1 includes an input 3 from a ventilator (not shown) to an adjustable selection valve, or shunt valve 4. Through a first outlet 10 of the shunt valve 4 the main part of the breathing gas is provided to a common line 17 that includes a reflecting filter 7. The common line is branched to an inspiration line 6 carrying breathing air to the patient and an expiration line 16 carrying expired air from the patient. The reflecting filter is arranged to adsorb anaesthetic agents exhaled by the patient so that it will not be evacuated with the bulk of the breathing gas. Instead, during the next inhalation the anaesthetic in the reflecting filter 7 will be desorbed and returned to the patient. A $CO_2$ absorber 9 is connected in series with the reflecting filter 7 in the inspiration line 6 between the reflecting filter 7 and the patient.

Through a second outlet 5 of the shunt valve 4 a smaller part of the breathing gas is provided to a vaporizer 11. Vaporized anaesthetic is provided from the vaporizer 11 to the inspiration line 6 between the absorbing filter and the patient. Between the vaporizer 11 and the patient a gas analyzer 13 is connected to the inspiration line 6 to monitor and control the composition of the gas, in particular the concentration of anaesthetic.

When in use, a Y-piece (schematically shown as 15) is used for connection to a patient, as is common in the art. The Y piece is connected, by means of hoses to the inspiration line 6 through a non-return valve 14a and to the expiration line 16 through a non-return valve 14b. The expiration line 16 and the inspiration line 6 are joined between the reflecting filter 7 and the $CO_2$ absorber 9. In this way, the reflecting filter 7 can adsorb anaesthetic from the expired air and desorb it again into the air to be inspired by the patient. The point of the inspiration line to which the Y piece is connected is referred to as the inspiration connection point 15a, and the point of the expiration line to which the Y piece is connected is referred to as the expiration connection point 16a From the reflecting filter 7 exhaled air is evacuated through the common line 17 to an evacuation line 33 for connection to a central evacuation/scavenging system or other exhaust gas retaining means (not shown). A positive end expiratory pressure (PEEP) valve 19 is connected in the common line near the evacuation line 33 for controlling the end expiratory pressure in the breathing circuit. Near the PEEP valve 19 on the breathing system side a manual ventilation bag 21 is connected through a manual ventilation valve 23. The evacuation line 33 is connected to a scavenging system (not shown) downstream of the PEEP valve 19. Technically, the PEEP valve is part of the ventilator, while all other components shown in FIG. 1 are included in the anaesthesia breathing circuit. The dashed line in FIG. 1 indicates the border between the ventilator on the left and the anaesthesia breathing circuit on the right of the dashed line.

In an alternative setup, not shown, the vaporizer block 11 may be connected in the inspiration line 6 between the $CO_2$ absorber 9 and the non-return valve 14a. The breathing gas from the shunt valve 4 is then introduced between the absorber and the vaporizer, or directly into the vaporizer. As will be shown in FIGS. 2 and 3 the apparatus is usually equipped with an external monitor. There are a number of components that are self evident in an anaesthesia circuit, but not shown, such as pressure and flow meters. These units provide data such as patient inspiratory and expiratory pressures and flows to a control unit.

The use of the apparatus in FIG. 1 is apparent to a person skilled in the art and will not be discussed in detail.

Figure 2:
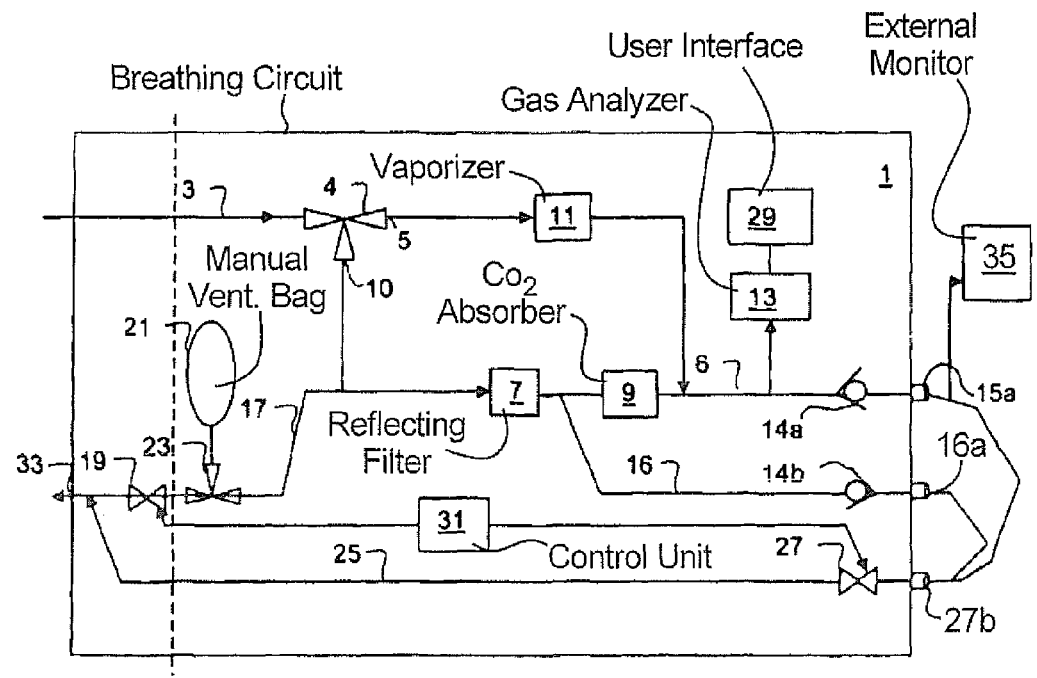
FIG. 2 shows the anaesthetic system of FIG. 1 modified for flushing the system according to a first embodiment of the invention.
Figure 3:
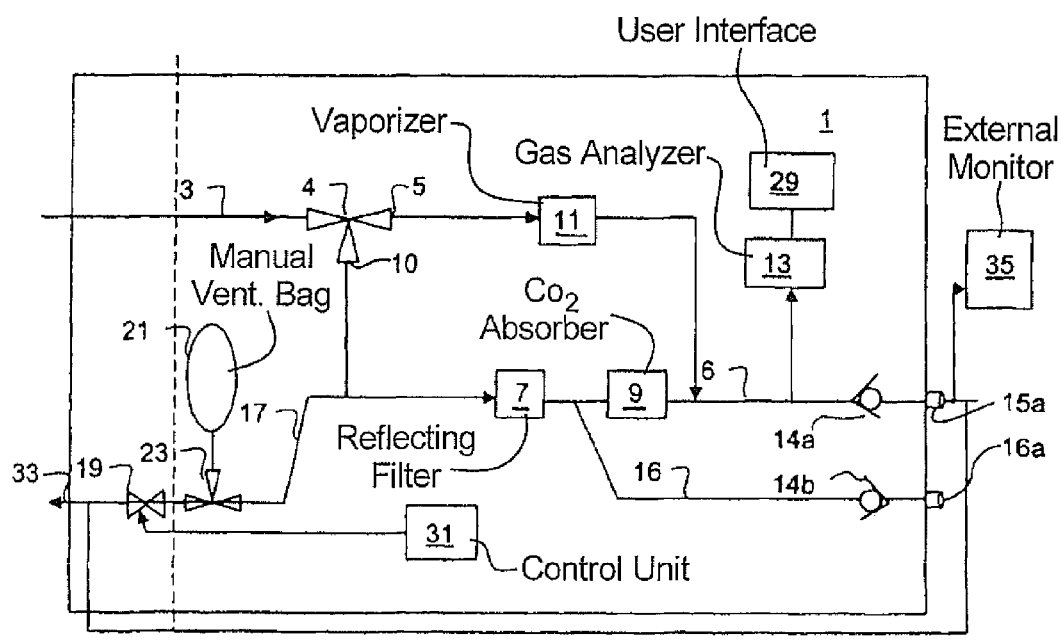
FIG. 3 shows the anaesthetic system of FIG. 1 modified for flushing according to a second embodiment of the invention.

FIGS. 2 and 3 show essentially the same anaesthetic apparatus as FIG. 1, but with modifications according to the invention, which enables flushing of the system to remove anaesthetics from the system between patients. Flushing is particularly important when a reflector filter and/or a $CO_2$ absorber is used, as most of the anaesthetic left in the system will be found in the reflector filter but also in the absorber, but may be useful in any kind of anaesthetic apparatus. As the skilled person will realize, the modifications made to the system for flushing and test, as described in connection with FIG. 2 and FIG. 3, can be made to any known anaesthetic system, for example, also to anaesthetic systems not comprising a reflecting filter, or a system in which the vaporizer is serially connected with the reflector and the absorber in the inspiration line. Also, of course, the ventilator (not shown) may provide a mixture of breathing gases FIG. 2 shows the same system as in FIG. 1 and with the same reference numerals used for the same elements in the drawing. In FIG. 2, the system has been modified for flushing according to a first embodiment of the invention. The inspiration connection point 15a and the expiration connection point 16a are both connected to an additional evacuation line 25 having an evacuation valve 27. Alternatively, the Y piece 15 may be kept and the end of the Y piece normally used for patient connection may be connected to the additional evacuation line 25. The additional evacuation line 25 is connected to the common evacuation line 33.

For flushing the system, a gas flow is provided through the shunt valve 4 both to the vaporizer 11 and to the reflecting filter 7 and $CO_2$ absorber 9. The non-return valve 14b prevents any flow of gas through the expiration line 16. The gas flushes the system as it passes through the various components and is returned through the evacuation valve 27 directly to the scavenging system. An example of a flushing procedure will described more in detail in conjunction to FIG. 4.

The gas analyzer 13 monitors the composition of the gas, and in particular the concentration and type of anaesthetic in the gas. The gas analyzer 13 is preferably connected to the user interface 29 arranged to indicate to the operator whether or not the anaesthetic apparatus is sufficiently flushed to use with a new patient. Preferably, the gas analyzer has a threshold value for the concentration of anaesthetic set either in the program or by the operator. When the measured concentration is below the threshold value the gas analyzer will determine that the flushing is completed.

This embodiment also enables flushing the manual ventilation bag 21 after use, and during pre-use check. By closing the PEEP valve 19 and the evacuation valve 27 the manual ventilation bag 21 can be filled with air. The PEEP valve 19 can then be opened to evacuate the manual ventilation bag 21. This procedure can be repeated as many times as necessary to flush the manual ventilation bag 21 from anaesthetic.

The setup shown in FIG. 2 can also be used during pre-use check to minimize the operator interaction needed. Instead of occluding the Y piece, as is commonly done at certain stages of pre-use check, the evacuation valve 27 can be closed to achieve the same effect. The inspiration line is then effectively connected to the expiration line and the system can be checked, for example, for leakages. A control unit 31 that executes a computer program could be provided for controlling the evacuation valve and the PEEP valve during pre-use check. The evacuation valve 27 is controlled in such a way that it is closed during the phases of pre-use check where the Y piece is occluded in conventional systems. The control unit 31 is shown as a separate unit but is suitably integrated in the control system of the anaesthetic apparatus 1. For simplicity, the control system is shown connected only to the PEEP valve 19 and the evacuation valve 27, but it is understood that the control unit 31 is preferably used to control other components of the anaesthetic apparatus as well, such as the shunt valve 4, are controlled by a processor based control system. Also, preferably, the control unit 31 is arranged to receive an input signal from the gas analyzer, indicating the concentration of anaesthetic agent in the gas flow. This input signal is preferably used by the control unit 31 to determine when the flushing may be stopped.

In case of a pre use check in-between patients, the operator may chose not to flush the anaesthesia apparatus under certain conditions. If the next patient is to be anesthetized with the same agent as the previous patient, it is possible to reuse the anaesthesia agent retained in the reflector. This is useful since the anaesthesia agent is ex-pensive.

As is common in the art, the common evacuation line 33 may be connected to a scavenging system (not shown) or to a carbon filter (not shown). The carbon filter will be particularly useful if the anaesthetic apparatus is being used, or flushed, or the pre use check is performed, in a place where no scavenging system is available, or if the scavenging system fails.

An external monitor 35 is shown connected to the ventilator to monitor and provide an indication of the anaesthetic concentration. The external monitor 35 is arranged to monitor the concentration at the Y piece near the patient. The external monitor 35 may be incorporated in the ventilator or may be a separate unit. While the internal gas analyzer is normally only used for internal measurements and control, the external monitor displays, on a graphical user interface, the concentration of the different components of the breathing gas inhaled and exhaled by the patient, such as $CO_2$, $O_2$, $N_2O$, and anaesthetic at the Y piece.

The apparatus according to the invention enables a function test of the external monitor 35 to be carried out, for example, before the flushing sequence. If gas having a known concentration is passed through the system the results from the internal analyzer 13 and the external gas monitor 35 can be compared. If the results match this is an indication that the external monitor functions correctly. Conversely, if the results differ, this indicates a functional error.

FIG. 3 shows an alternative embodiment, in which the inspiration connection point 15a is connected directly to the evacuation line 33. The expiration connection point 16a is closed. As before, the evacuation line 33 may be connected to a carbon filter (not shown) or a scavenging system (not shown). Of course, the inspiration connection port may be connected directly to a scavenging system or a carbon filter without being connected to the evacuation line 33, although this will result in a more complicated and less feasible solution.

Even though no gas can flow through the expiration line 16 in the embodiment shown in FIG. 3, the expiration line 16 will still be cleaned of anaesthetic agent to the extent necessary through diffusion. This part of the breathing circuit is very small compared to the rest of the breathing circuit, and contains much less anaesthetic agent than the reflector filter 7. The control unit 31 is arranged to control the PEEP valve 19 and the shunt valve 4.

As in FIG. 2 the gas analyzer 13 monitors the composition of the gas, and in particular the concentration of anaesthetic in the gas. The gas analyzer 13 is preferably connected to a user interface 29 arranged to indicate to the operator whether or not the anaesthetic apparatus is sufficiently flushed to use with a new patient. There is also an external monitor 35 used in the same way as in FIG. 2.

Figure 4:
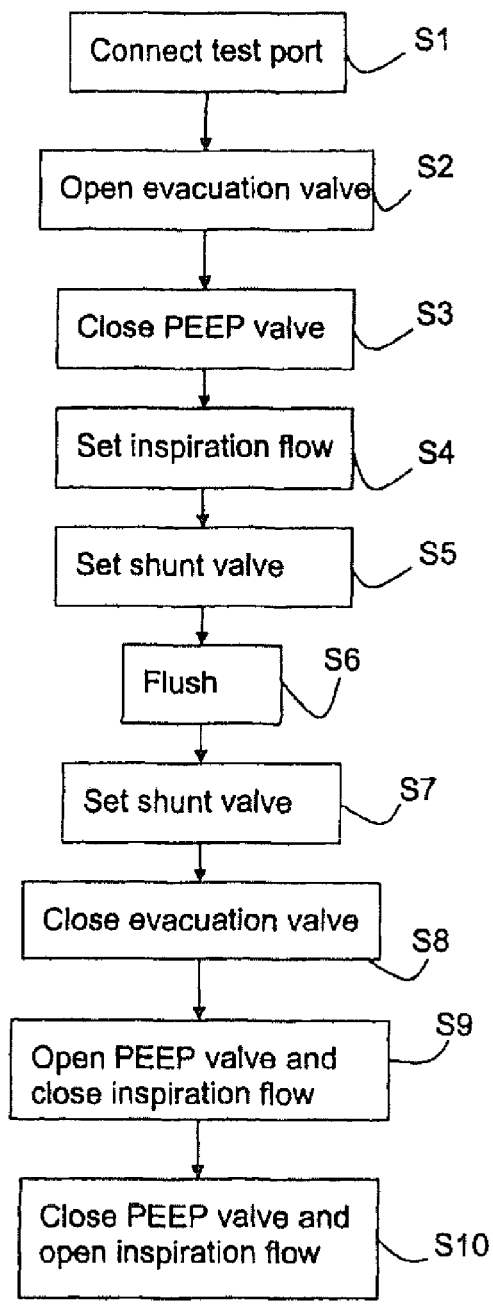
FIG. 4 is a flow chart of a flushing sequence that may be performed in an apparatus according to the present invention.

In the embodiment shown in FIG. 2, the flushing sequence may be carried out, for example, as illustrated in FIG. 4.
 Step S1: Connect the Y piece to a test port 27b.
 Step S2: Open the evacuation valve 27.
 Step S3; Close the PEEP valve 19.
 Step S4: Set the inspiration flow to an appropriate value, for example approx. 20 l/min (The flow must not exceed the evacuation capacity of the scavenging system, normally about 25 l/min).

Step S5: Position the shunt valve 4 to distribute the gas appropriately between the first and second outlets, for example, to 10% through the second outlet 5 and 90% through the first outlet 10.

Step S6: Flush gas through the system until the analyzer 13 indicates an acceptable concentration of anaesthetics. The analyzer 13 may compare the concentration to a threshold value to determine when it is acceptable.

The main part of the breathing circuit is now free of anaesthetic agent. It is now possible to clear the manual ventilation bag.

Step S7: Position the shunt valve to 100% through the first outlet 10.

Step S8: Close the evacuation valve 27 and open the manual ventilation valve 23 to access the manual ventilation bag 21.

Step S9: Open the PEEP valve 19 when the circuit pressure reaches a preset level and close the inspiration flow 3 until the circuit pressure has reached a lower preset level to allow the manual bag to be flushed. Typically, the upper level could be any-where in the range 20-50 cmV, for example 30 cmV, and the lower level near 0 cmV. The actual values are not critical as long as the upper limit does not damage the manual bag.

Step S10: Close the PEEP valve 19 and open the inspiration flow.

Steps S9 and S10 are preferably repeated an appropriate number of times, until the manual bag 21 is sufficiently free of anaesthetic agent. This may be determined by means of a gas analyzer sampling the gas between the PEEP valve and the manual ventilation valve 23. Alternatively the appropriate number of times may be estimated or determined by empirical tests.

As those skilled will realize, FIGS. 2 and 3 illustrate the principle of the invention applied to a particular anaesthetic apparatus. Therefore, these figures are only intended as examples of how such an apparatus may be implemented. The invention may be applied to any type of anaesthetic apparatus, although it will be particularly useful in anaesthetic apparatuses comprising an adsorption/desorption filter 7. Of course the detailed control of the gas flow may to some extent depend on the actual implementation of the breathing circuit.

In both the embodiments shown a heater (not shown) may be included for heating the reflector filter to change its adsorption properties so that the anaesthetic agent will be desorbed more easily.

Although modifications and changes may be suggested by those skilled in the art, it is the intention of the inventors to embody within the patent warranted heron all changes and modifications as reasonably and properly come within the scope of their contribution to the art.

We claim as our invention:

1. An anaesthesia apparatus comprising an inspiration line and an expiration line, connectable to and disconnectable from a patient, at least one gas source that provides breathing gas to the inspiration line, a vaporizer that provides vaporized anaesthetic to the inspiration line, a $CO_2$ absorber in the inspiration line, a common line that transports breathing gas and expired gas, and an evacuation line for expired gas for connection to an evacuation system, said evacuation line comprising a PEEP valve, and a control unit that controls a gas flow of a flushing gas through at least part of the anaesthesia apparatus to flush anaesthetic agent from the apparatus automatically when the expiration line and the inspiration line are not connected to the patient.

2. An anaesthesia apparatus according to claim 1, further comprising an evacuation system connected to said evacuation line for evacuating the flushing gas.

3. An anaesthesia apparatus according to claim 1, further comprising a reflector filter in a breathing circuit that reflects exhaled anaesthetic agent during connection to a patient, wherein the control unit controls the gas flow through the reflector filter to flush any anaesthetic agent from the filter when the expiration line and the inspiration line are not connected to the patient.

4. An anaesthesia apparatus according to claim 3, wherein the reflector filter is connected upstream of the $CO_2$ absorber.

5. An anaesthesia apparatus according to claim 1, further comprising a gas analyzer that monitors concentration of anaesthetic in the gas that provides a signal indicative of the concentration to the control unit, the control unit controlling the gas flow in dependence on said signal.

6. An anaesthesia apparatus according to claim 1, comprising a second evacuation line for connection to an evacuation system.

7. An anaesthesia apparatus according to claim 6, wherein the second evacuation line is connected between a patient end of the inspiration line and the evacuation line, said second evacuation line comprising an evacuation valve.

8. An anaesthesia apparatus according to claim 6, comprising a carbon filter connectable to the evacuation line.

9. An anaesthesia apparatus according to claim 1, further comprising a manual ventilation system connected to the evacuation line near the PEEP valve on a breathing system side.

10. An anaesthesia apparatus according to claim 1, wherein the control unit performs the flushing as part of a pre-use check.

11. A method of operating an anaesthesia apparatus, said anaesthesia apparatus comprising an inspiration line and an expiration line, said expiration line comprising a PEEP valve, at least one gas source for providing breathing gas to the inspiration line, a vaporizer for providing anaesthetic to the inspiration line, and a common line for transporting breathing gas and expired gas, and an evacuation line for evacuating expired gas, said method comprising the step of providing a gas flow of a flushing gas through at least part of the anaesthesia apparatus as to flush anaesthetic agent from the apparatus automatically when the apparatus is not connected to a patient.

12. A method according to claim 11 comprising the step of evacuating the flushing gas through an evacuation means.

13. A method according to claim 11, the apparatus further comprising a reflector filter in a breathing circuit, said method comprising the step of controlling the gas flow to flush the reflector filter by means of the flushing gas when the apparatus is not connected to the patient.

14. A method according to claim 11, further comprising the step of monitoring the concentration of anaesthetic in the flushing gas with a gas analyzer and determining when the flushing is completed based on the monitored concentration.

15. A method according to claim 11, comprising flushing the flushing gas through a second evacuation line to a scavenging system.

16. A method according to claim 11, comprising flushing the flushing gas through a second evacuation line to a carbon filter.

17. A method according to claim 11, the anaesthesia apparatus further comprising a second evacuation line connected between a patient end of the inspiration line and the evacuation line for evacuation of the gas, said second evacuation line comprising an evacuation valve, further comprising the steps:

opening the evacuation valve;
closing the PEEP valve;
setting inspiration flow to an appropriate value;

flushing gas through at least a part of the system until the analyzer indicates an acceptable concentration of anaesthetics.

18. A method according to claim 17, further comprising the steps of:

closing the evacuation valve (27);

opening the PEEP valve when the circuit pressure reaches a preset level and stopping the inspiration flow until the circuit pressure has reached a lower preset level; and closing the PEEP valve and opening the inspiration flow.

19. A method according to claim 18, comprising repeating the two last steps are repeated until the system is sufficiently free of anaesthetic gas.

20. A method according to claim 11, comprising performing the flushing as part of a pre-use check.

21. A computer-readable medium encoded with programming instructions, said computer-readable medium being loadable into a control unit of an anaesthesia apparatus comprising an inspiration line and an expiration line, said expiration line comprising a PEEP valve, at least one gas source for providing breathing gas to the inspiration line, a vaporizer for providing anaesthetic to the inspiration line, and a common line for transporting breathing gas and expired gas, and an evacuation line for evacuating expired gas, said programming instructions causing said control unit to:

provide a gas flow of flushing gas through at least a part of the anaesthesia apparatus to flush anaesthetic agent from the apparatus automatically when the apparatus is not connected to the inspiration line and the expiration line.

22. A computer-readable medium as claimed in claim 21 wherein said programming instructions further cause said control unit to execute said flushing in a pre-use check of said anaesthesia apparatus.

\* \* \* \* \*